United States Patent
Cheung et al.

(10) Patent No.: US 10,639,204 B2
(45) Date of Patent: May 5, 2020

(54) SURGICAL COMPONENT NAVIGATION SYSTEMS AND METHODS

(71) Applicant: X-Nav Technologies, LLC, Lansdale, PA (US)

(72) Inventors: Andrew Cheung, Knoxville, TN (US); Joshua Campbell, Knoxville, TN (US)

(73) Assignee: X-Nav Technologies, LLC, Lansdale, PA (US)

( * ) Notice: Subject to any disclaimer, the term of this patent is extended or adjusted under 35 U.S.C. 154(b) by 397 days.

(21) Appl. No.: 14/879,612

(22) Filed: Oct. 9, 2015

(65) Prior Publication Data

US 2016/0030132 A1 Feb. 4, 2016

Related U.S. Application Data

(63) Continuation of application No. 13/214,783, filed on Aug. 22, 2011, now abandoned, which is a
(Continued)

(51) Int. Cl.
*A61F 13/00* (2006.01)
*A61B 34/20* (2016.01)
(Continued)

(52) U.S. Cl.
CPC ........ *A61F 13/00068* (2013.01); *A61B 34/20* (2016.02); *A61C 1/082* (2013.01);
(Continued)

(58) Field of Classification Search
CPC ....... A61F 13/00068; A61F 2013/0017; A61B 34/20; A61B 2034/2051;
(Continued)

(56) References Cited

U.S. PATENT DOCUMENTS

| 5,772,594 A | 6/1998 | Barrick |
| 5,921,992 A | 7/1999 | Costales et al. |

(Continued)

OTHER PUBLICATIONS

Patwari, Location Estimation in Sensor Networks. The univeristy of Michigan, 2005, [URL:http://web.eecs.umich.edu/~hero/Preprints/patwari_thesis_final.pdf] entire document.
(Continued)

*Primary Examiner* — Joseph M Santos Rodriguez
(74) *Attorney, Agent, or Firm* — Faegre Drinker Biddle & Reath LLP

(57) ABSTRACT

A navigation and monitoring system to track positions of surgical components during surgery of a patient. Some embodiments include a power source to emit a tracking signal during surgery of the patient, a first sensor mounted to a region of the patient to respond to the emitted tracking signal, and a control unit to track a position of the region relative to a fixed region of the patient as the region moves with respect to the fixed region, based on the response of the first sensor. The system can calibrate and register a movable reference point of the patient relative to a fixed reference point, and can maintain that reference point when the movable reference point moves in space during a surgical process.

10 Claims, 9 Drawing Sheets

Related U.S. Application Data continuation-in-part of application No. 12/860,635, filed on Aug. 20, 2010, now abandoned.

(51) Int. Cl.
  *A61C 1/08* (2006.01)
  *G01S 5/02* (2010.01)
  *G01S 17/06* (2006.01)
  *G02B 27/01* (2006.01)

(52) U.S. Cl.
  CPC .............. *A61C 1/084* (2013.01); *G01S 5/0294* (2013.01); *G01S 17/06* (2013.01); *G02B 27/017* (2013.01); *A61B 2034/2051* (2016.02); *A61B 2034/2055* (2016.02); *A61F 2013/0017* (2013.01)

(58) Field of Classification Search
  CPC .......... A61B 2034/2055; G02B 27/017; G01S 5/0294; G01S 17/06; A61C 1/082; A61C 1/084
  See application file for complete search history.

(56) References Cited

U.S. PATENT DOCUMENTS

| | | | |
|---|---|---|---|
| 5,989,023 | A | 11/1999 | Summer et al. |
| 6,081,741 | A | 6/2000 | Hollis |
| 6,096,050 | A | 8/2000 | Audette |
| 6,226,548 | B1 | 5/2001 | Foley et al. |
| 6,348,058 | B1 | 2/2002 | Melkent et al. |
| 6,434,507 | B1 | 8/2002 | Clayton et al. |
| 6,450,978 | B1 | 9/2002 | Brosseau et al. |
| 6,470,207 | B1 | 10/2002 | Simon et al. |
| 6,474,341 | B1 | 11/2002 | Hunter et al. |
| 6,490,467 | B1 | 12/2002 | Bucholz et al. |
| 6,491,699 | B1 | 12/2002 | Henderson et al. |
| 6,592,531 | B2 | 7/2003 | Bonutti |
| 6,827,723 | B2 | 12/2004 | Carson |
| 7,319,540 | B2 | 1/2008 | Tipirneni |
| 7,346,417 | B2 | 3/2008 | Luyth et al. |
| 7,386,339 | B2 | 6/2008 | Strommer et al. |
| 7,392,076 | B2 | 6/2008 | De La Barrera |
| 7,398,116 | B2 | 7/2008 | Edwards |
| 7,559,935 | B2 | 7/2009 | Solar et al. |
| 7,638,958 | B2 | 12/2009 | Philipps et al. |
| 7,751,865 | B2 * | 7/2010 | Jascob ................ A61B 5/06 128/899 |
| 2004/0087852 | A1 | 5/2004 | Chen et al. |
| 2004/0171930 | A1 | 9/2004 | Grimm et al. |
| 2005/0085714 | A1 * | 4/2005 | Foley ................ A61B 17/1735 600/424 |
| 2005/0113659 | A1 | 5/2005 | Pothier et al. |
| 2005/0182449 | A1 * | 8/2005 | Auge, II ................ A61B 18/14 607/3 |
| 2006/0058919 | A1 | 3/2006 | Sommer |
| 2007/0106152 | A1 * | 5/2007 | Kantrowitz .......... A61N 5/1049 600/424 |

OTHER PUBLICATIONS

Abreau et al., Real-Time Wireless Location and Tracking System with Motion Pattern Detection; InTech. Mar. 2010 http://cdn.intechweb.org/pdfs/10580.pdf]; Re.

* cited by examiner

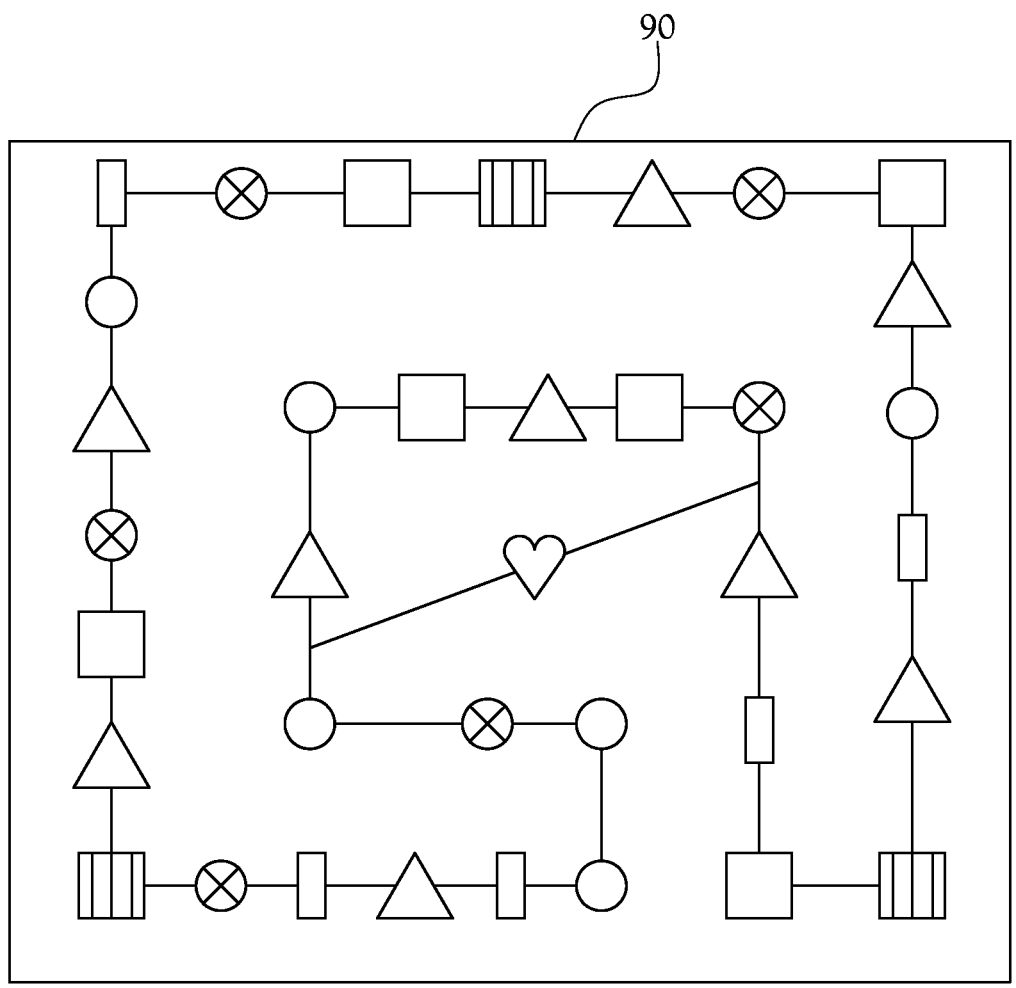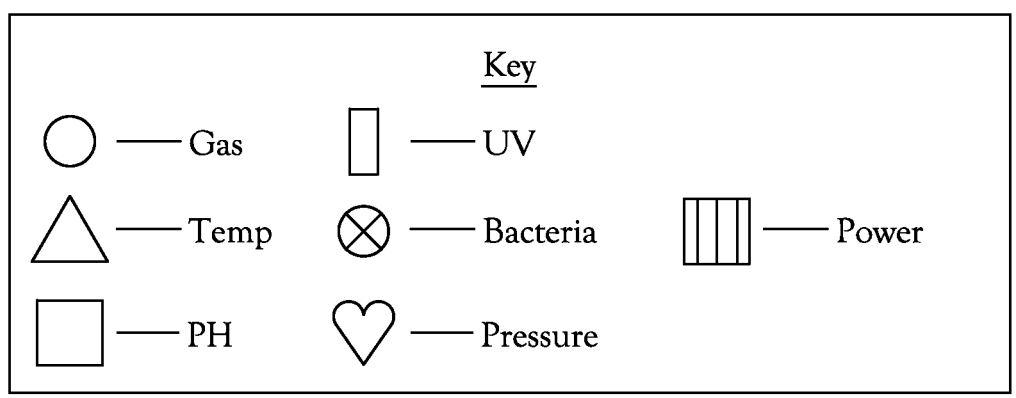
Fig.9

SURGICAL COMPONENT NAVIGATION SYSTEMS AND METHODS

CROSS-REFERENCE TO RELATED APPLICATIONS

This application is a continuation of U.S. application Ser. No. 13/214,783 filed on Aug. 22, 2011, which is a continuation-in-part of U.S. application Ser. No. 12/860,635 filed on Aug. 20, 2010, the contents of which are incorporated by reference herein in their entirety.

BACKGROUND OF THE INVENTION

1. Field of Invention

The present general inventive concept relates generally to navigation of surgical components and, more particularly, to systems and methods to assist a surgeon in navigating anatomical regions of a patient to properly position and locate surgical components, adjuncts, surgical guides, goggles, dressings, instruments, and other surgical components before, during, and after injury or surgery of a patient, and for navigation and use around wounds and surgical sites.

2. Description of the Related Art

The controlled positioning of surgical instruments and other components is of significant importance in many surgical procedures and wound care applications, and various methods and navigation systems have been developed to navigate surgical components relative to a patient during surgery. Intra-operative navigation systems are comparable to global positioning satellite (GPS) systems commonly used in automobiles and are composed of three primary components: a localizer, which is analogous to a satellite in space; an instrument or surgical probe adjunct, guide, goggle, or dressing, which represents the track waves emitted by the GPS unit in the vehicle; and CT scan and/or other data sets such as MRI, PET/CT, or optical data sets that are analogous to a road map of the anatomical structure of the patient. These image navigation techniques generally allow positioning of a surgical instrument within a margin of error of about 1 to 2 mm, or sub mm accuracy depending on the scan.

Computer assisted image guidance techniques typically involve acquiring preoperative images of the relevant anatomical structures and generating a data base which represents a three dimensional model of the anatomical structures. The position of the instrument relative to the patient is determined by the computer using at least three fixed reference elements that span the coordinate system of the object in question. The process of correlating the anatomic references to the digitalized data set constitutes the registration process. The relevant surgical instruments or other components and surgical sites typically have a known and fixed geometry which is also defined preoperatively. During the surgical procedure, the position of the component being used is registered with the anatomical coordinate system and a graphical display showing the relative positions of the tool and anatomical structure may be computed and displayed to assist the surgeon in properly positioning and manipulating the surgical component with respect to the relevant anatomical structure.

One of the disadvantages of known systems is the need to maintain proper positioning of surgical instruments relative to movable anatomic references when those references are moved during surgery, and to enable surgeons to properly position surgical instruments in real time when anatomical reference points are moved during surgery.

BRIEF SUMMARY OF THE INVENTION

The present general inventive concept provides systems and methods to digitally register and track movable regions of a patient, enabling a surgeon to accurately position and navigate surgical components such as, but not limited to, surgical instruments, adjuncts, guides, goggles, wound dressings, and other surgical components with respect to reference points even when the reference points are moved before, during, or after treatment or surgery.

Additional features and embodiments of the present general inventive concept will be set forth in part in the description which follows and, in part, will be obvious from the description, or may be learned by practice of the general inventive concept.

Example embodiments of the present general inventive concept can be achieved by providing a navigation system to track positions of surgical components before, during, or after an operation of a patient, including a power source to emit a detectable signal during operation of a patient, a first sensor mounted to a movable region of the patient to respond to the emitted signal, and a control unit to track a position of the movable region relative to a fixed region of the patient as the movable region moves with respect to the fixed region, based on the response of the first sensor.

The navigation system can include a second sensor mounted to a surgical component to respond to the emitted signal such that the control unit tracks a position of the surgical component relative to the movable region as the surgical component and movable region move with respect to the fixed region, based on the responses of the first and second sensors.

Example embodiments of the present general inventive concept can also be achieved by providing a navigation system to track positions of surgical components before, during, or after an operation of a patient, including a detection unit to detect an LED or electromagnetic signal, a first sensor mounted to a movable region of the patient to emit a first LED or electromagnetic signal to be detected by the detection unit, and a control unit to track a position of the movable region relative to a fixed region of the patient as the movable region moves with respect to the fixed region, based on the detected first LED or electromagnetic signal.

Example embodiments of the present general inventive concept can also be achieved by providing a method of tracking positions of surgical components before, during, or after an operation of a patient, including emitting tracking signals to a targeted region of a surgical site, coupling a first sensor to a movable region of the patient such that the first sensor responds to the emitted tracking signals, and tracking a position of the movable region relative to a fixed region of the patient as the movable region moves with respect to the fixed region, based on the response of the first sensor.

Example embodiments of the present general inventive concept can also be achieved by providing a navigation system to track positions of surgical components during surgery of a patient, including a power source to emit a tracking signal during surgery of a patient, a first sensor mounted to a region of the patient to generate a first response signal to the emitted tracking signal, a second sensor mounted to a surgical component to generate a second response signal to the emitted tracking signal, and a control unit to track a position of the surgical component relative to the region as the surgical instrument and region move with respect to a fixed region of the patient, wherein the tracked position is based on a triangulation calculation relative to the first and second response signals independent of a shape dimension of the first and second sensors.

The first sensor can be a digital scanner to read data pertaining to a region of interest of the patient to adjust existing CT scan data of the patient.

The navigation system can include a set of navigation goggles worn by a surgeon to display in real-time the position of the surgical component and/or region during surgery.

Example embodiments of the present general inventive concept can also be achieved by providing a navigation system to track positions of surgical components, including a power source to emit a tracking signal during an operation of a patient, a first component mounted to a region of interest of the patient, the first component including a first sensor to respond to the emitted tracking signal to provide location information of the first component, a second component including a second sensor to respond to the emitted tracking signal to provide location information of the second component, and a control unit to track the locations of the first and second components relative to a fixed region of the patient as the first or second components move with respect to the fixed region based on the responses of the first and second sensors, independent of a shape dimension of the first or second sensors.

Example embodiments of the present general inventive concept can also be achieved by providing a wound care device to monitor and treat wounds of a patient, including a dressing to cover a wound of a patient, at least one detector to measure a characteristic parameter of the wound, and to transmit a signal representative of the measured characteristic parameter, and a control unit to receive the transmitted signal and to output a response indicative of the measured characteristic parameter to treat the wound.

The monitoring device can include a sensor device to facilitate calculation of location information of the monitoring device. The monitoring device can be part of the navigation system or can be used as a separate component to monitor and treat wounds.

BRIEF DESCRIPTION OF THE SEVERAL VIEWS OF THE DRAWINGS

The above-mentioned features of the present general inventive concept will become more clearly understood from the following detailed description read together with the drawings in which:

FIG. 9 illustrates an exemplary wound dressing including a plurality of sensors to aid in navigation and detection of a variety of parameters to assist in treatment of the wound, according to an example embodiment of the present general inventive concept.

DETAILED DESCRIPTION OF THE INVENTION

Figure 1:
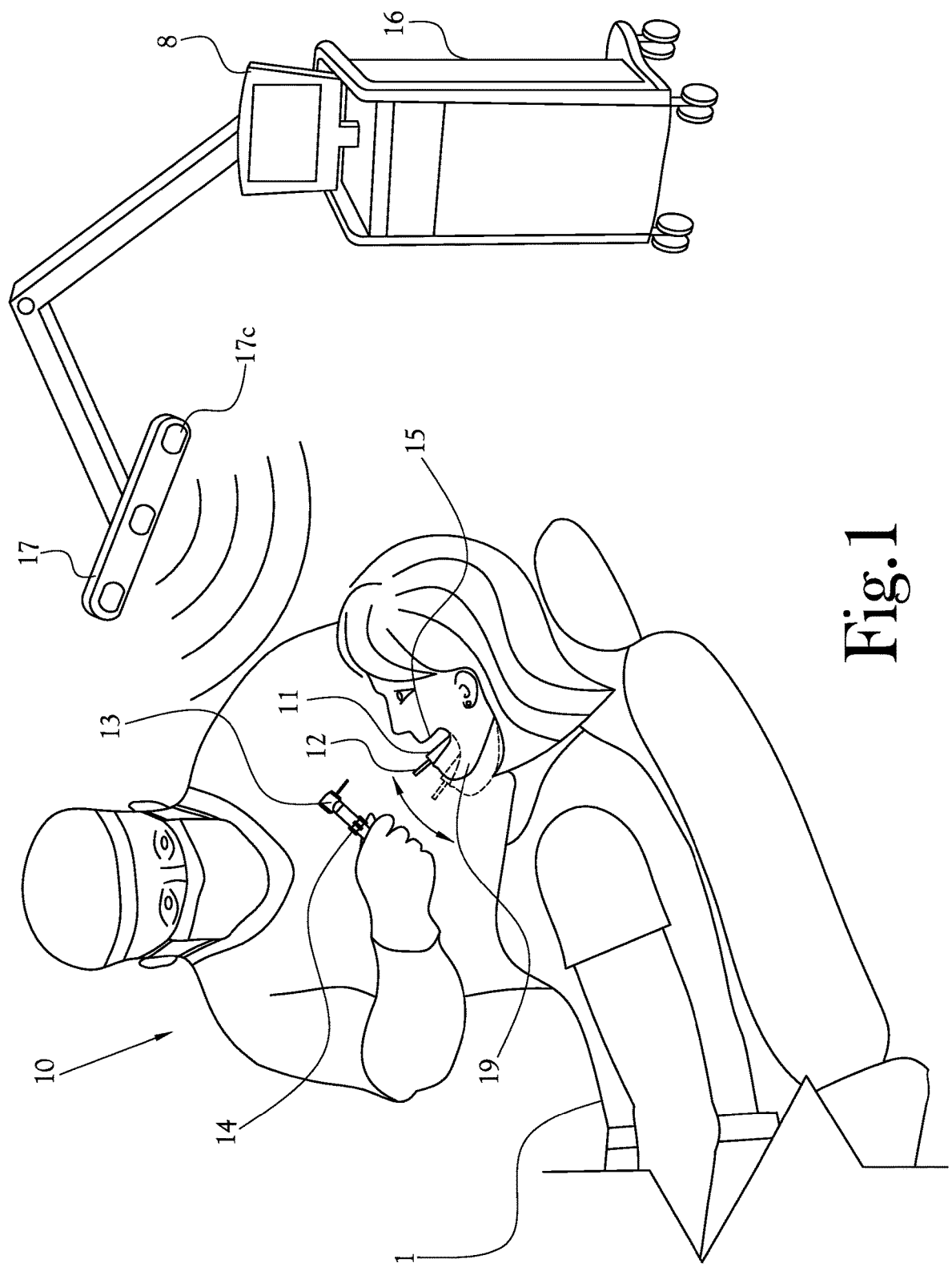
FIG. 1 is a perspective view of a system environment in which the features of the present general inventive concept may be implemented.

Reference will now be made to various embodiments of the present general inventive concept, examples of which are illustrated in the accompanying drawings, wherein like reference numerals refer to like elements throughout. The following description of the various embodiments is merely exemplary in nature and is in no way intended to limit the present general inventive concept, its application, or uses. The example embodiments are merely described below in order to explain the present general inventive concept by referring to the figures.

The present general inventive concept provides systems and methods of navigating surgical components with respect to anatomical regions of a patient, and assisting a surgeon in locating anatomical regions of a patient to properly position and locate surgical components such as, but not limited to, surgical adjuncts, surgical guides, goggles, dressings, and other surgical instruments and treatment components before, during, and after injury or surgery of a patient, and for navigation and use around surgical sites. As used herein, the term surgical components is intended to encompass, but is not limited to, all surgical devices, instruments, and components for use in navigation around wound sites, whether used before, during, or after surgery or treatment thereof.

In some embodiments, the navigation system enables a surgeon to track a location of a movable reference point relative to a fixed reference point as the movable reference point moves in space with respect to the fixed reference point during a surgical procedure.

The techniques of the present general inventive concept can be implemented in conjunction with robots to provide reference in space for surgical components and wound locations to aid in precision surgery.

In some embodiments, the navigation system utilizes known GPS triangulation methods to determine the location of sensors on both the patient's body and the surgical component, independent of the shape or size of the sensors.

FIG. 1 is a perspective view illustrating an exemplary system environment in which the features of the present general inventive concept may be implemented. The system environment of FIG. 1 includes a navigation system generally indicated by reference number 10 to navigate surgical instruments with respect to targeted anatomical structures of a patient 1. The simplified diagram of FIG. 1 illustrates a drilling instrument 13 for use in an oral surgery procedure and a patient 1. In FIG. 1, the patient is prepared for oral surgery toward a targeted region of the patient's mandible 19. As illustrated in FIG. 1, the mandible 19 is a movable anatomical structure as generally indicated by the phantom lines and direction arrow in FIG. 1. Since the mandible 19 is movable with respect to a fixed reference point such as the patient's skull or maxilla 15, the mandible 19 is referred to as a movable region or movable reference point. However, the present general inventive concept is not limited to any particular anatomical structure or type of movable reference point, nor is it limited to oral surgery procedures. Those skilled in the art will appreciate that many other anatomical structures could be used as a movable reference depending on the location and scope of the targeted surgical region, such as head, legs, arms, feet, hands, etc. Accordingly, the present general inventive concepts can be used to navigate any type of surgical or medical/dental instrument or component, for example, endoscopic systems, suction devices, screw devices, guides, wires, syringes, needles, drug delivery systems, biopsy systems, arthroscopic systems, wound dressings, etc. Furthermore, embodiments of the present general inventive concept may be used to navigate and/or treat any targeted region or anatomical structure of the patient's body during any medical or dental procedure, internally or externally, in addition to surgery on the mandible region as illustrated in FIG. 1. It is noted that the simplified diagram does not illustrate various connections, for example, power, ground, and interface connections to the various components; however, those skilled in the art will recognize the need for such connections and understand how to implement such connections, based on the components ultimately selected for use.

Referring to FIG. 1, the navigation system 10 includes a surgical aid device such as movable guide member 11, a power source or emitting device 17, and a control unit 16 having a display monitor 8. In some embodiments, the movable guide member 11 can be a customized guide fitted to individual cusps of the teeth including sensors to provide triangulation information for use in navigating craniofacial or dental operations. The system may also include a surgical component such as 13 to be tracked with respect to the location of a surgical site of interest as represented by movable guide member 11. The movable guide member 11 and surgical instrument 13 can include sensor elements 12 and 14, respectively. The emitting device 17 emits a propagating signal to communicate with the sensors 12 and 14 to track the location of the surgical instrument 13 relative to the movable guide member 11. Thus, using a customized guide member 11, for example, it is possible to use the patient's teeth or dental alveolus as unique registration points (e.g., fixed points) to register the mouthpiece/guide 11 during oral surgery. It is also possible to form other shapes and sizes of guide members, such as but not limited to guidance screws, implants, bandages, dressings, drapes, and the like, and attach them to other body parts to provide registration points for other parts of the body during other types of surgeries.

The emitting device 17 may also include a detection unit 17c to detect responses of the sensors 12, 14. Once the responses are detected by the detection unit 17c, the control unit 16 utilizes a multi-triangulation concept to calculate the position of the sensors 12 and 14 based on the detected responses to tracking signals emitted by the emitting device 17. The manner in which the emitting device 17 and/or detection unit 17c communicates with the sensors 12 and 14 to track the position thereof is well known in the art and is therefore only described generally. In some embodiments, it is possible that the functions of the emitter 17 and sensors 12 and 14 may be reversed and/or combined using sound engineering judgment to achieve the same or similar results. For example, it is possible for the sensors 12 and 14 to function as emitters rather than sensors, and it is possible for the emitter 17 to function as a sensor rather than an emitter. In any case, it is possible to utilize known triangulation methods to calculate and track the positions of the sensors 12 and 14 relative to the targeted surgical field using the configurations and techniques of the present general inventive concept. In other embodiments, the navigation system 10 may include an optional imaging device (not illustrated), such as an MRI unit, CT scanner, or other type of imaging device, optical device, or electromagnetic device, to acquire pre-, intra-, or post-operative or real-time images of the patient 1, in order to determine location coordinates with respect to a fixed portion of the patient's body, for example, to obtain digital coordinates of the various components relative to the patient's maxilla or skull region 15.

Referring to FIG. 1, the emitting device 17 can generate a tracking signal which can be received by sensors 12 and/or 14. The tracking signal may take the form of an infrared light signal (IR), electromagnetic (EM) signal, Bluetooth signal, Wi-Fi signal, or other known or later developed wired or wireless signal. In the example embodiment of FIG. 1, it is presumed for convenience of description that the propagating signal is an LED light signal transmitted from the emitting device 17 to the sensors 12 and 14. In this embodiment, in order to track the location of the guide member 11 and/or surgical component 13, the sensors 12 and 14 can function as reflecting markers to transmit light signals received from the emitting device 17 to a detection unit 17c, such as a CCD camera device. Using the reflected LED signals, the detection unit 17c can determine the location of the sensors 12 and 14 based on characteristics such as intensity, refraction angle, etc. of the reflected LED signals, and can inform the control unit 16 of the location of the sensors in real time based on the characteristics of the reflected LED signals. In other embodiments, it is possible that the sensors 12 and 14 can include one or more emitting devices to emit LED signals directly from the sensors to the detection unit 17c. In this case, the position of the sensors 12, 14 can be directly tracked by the detection unit 17c by detecting and characterizing the LED signals emitted from the sensors directly, in which case the emitting device 17 may not be required. Those skilled in the art will appreciate that many other configurations and combinations of elements in addition to those illustrated in FIG. 1 could be used without departing from the broader scope of the present general inventive concept.

During typical dental or medical procedures, the patient's MRI or CT scans may be fed into the control unit 16 to compare the scanned MRI or CT images to anatomical landmarks or reference points fixed on the patient's head and face to calibrate a location of the fixed reference point relative to a target point for the procedure or surgery. In the embodiment of FIG. 1, the patient's maxilla 15 can be used as a fixed reference point. To register the fixed reference point, it is possible to calculate a position of the fixed reference point with respect to the targeted surgical field (e.g., mandible region) based on coordinates of the patient generated by the MRI or CT scans. It is also possible to directly register a location of the fixed reference point by mounting a fixed device, such as a screw device (not illustrated), adapted to include an integrated sensor device to correspond and define a fixed reference point of the patient's skull. The fixed sensor device can then be used to communicate with the emitting device 17 and/or detection unit 17c to calibrate the location of the fixed reference point relative to one or more other sensors or reference points of the patient. In this way, the fixed reference point 15 may be used as a positional reference frame to determine the relative position of the surgical component 13 with respect to the target point of the surgery, and to calibrate a position of the movable guide element 11.

To carry out a particular surgical process, it may be important to move the patient's mandible 19 during the process as indicated by the phantom lines and direction arrow illustrating movement of the mandible 19 as depicted in FIG. 1. Here, the surgeon can attach a surgical aid component such as a movable guide member 11 adapted with a sensor array 12 to a portion of the patient's mandible to track movements of the patient's mandible 19, as illustrated in FIG. 1.

Figure 2A:
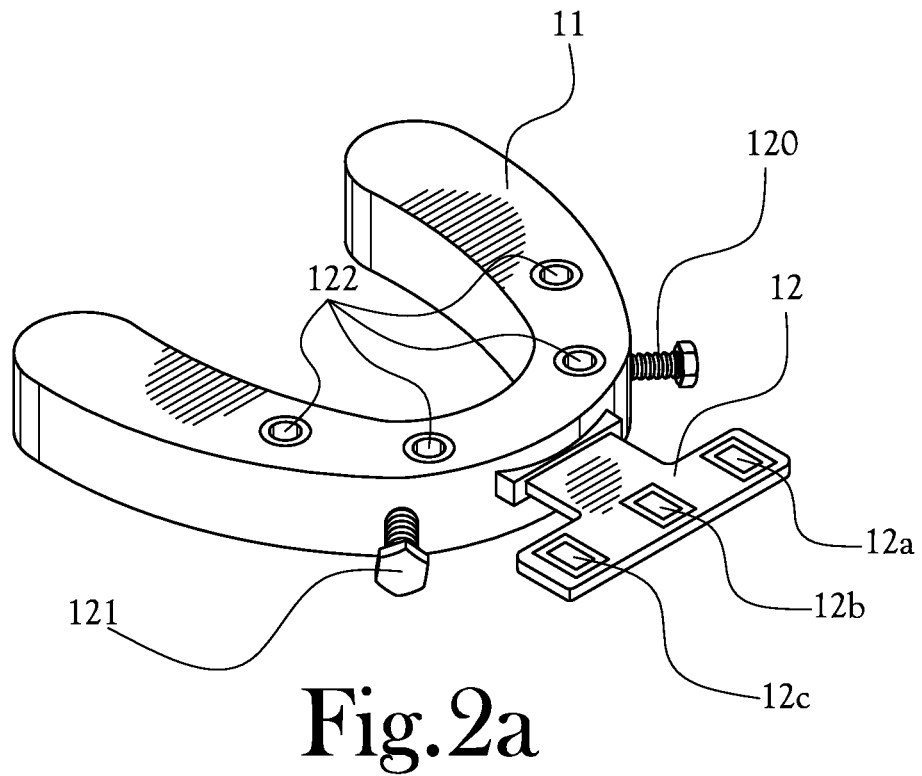
FIG. 2A is a perspective view of an exemplary guide member including optical sensor members in accordance with an example embodiment of the present general inventive concept.

Referring to FIGS. 1 and 2A, the exemplary movable guide member 11 can be configured in the shape of a semicircular mouthpiece to fit precisely on the patient's mandible. The movable guide member 11 typically includes a series of holes 122 which the surgeon uses to locate and orient dental implants during oral surgery. The movable guide member 11 can be attached to the patient's mandible by way of fasteners 120 and 121. The fasteners 120, 121 may take the form of fixation screws, bolts, or pins, but the present general inventive concept is not limited thereto. Many other types of fastening devices or glues may be used to attach a guide member 11 and sensor 12 to these and/or other movable regions of the patient without departing from the broader scope of the present general inventive concept. For example, fixation methods such as intermaxillary fixation (IMF) methods, IMF screws, and the like, can be adapted to include a sensor device in accordance with the present general inventive concept to track movements of a movable region of the patient during a medical or dental procedure. It is possible to mount a sensor 12 to a guide member such as a bite plate device and/or customized guide based on the individual unique cusps of teeth, secured to a lower jaw of the patient by screws. This facilitates using the teeth and/or dental alveolus as unique registration points (fixed points) to register the location of the mouthpiece/ guide during oral surgery. It is possible to use other body parts and attachment devices, chosen with sound engineering judgment, to assist with other types of surgeries or treatment operations. Moreover, although the example embodiment of FIG. 2A illustrates a mouthpiece-shaped guide member 11 to incorporate the sensor 12, the present general inventive concept is not limited to such configuration, and various other types of sensor arrangements may be used in connection with a variety of other types of fixation devices, methods, or splints to track and maintain a movable reference point during surgery. For example, it is possible to incorporate a sensor device into a locating pin or other fastening device, such as a surgical screw, and to attach the pin or screw to the targeted movable region of the patient to track the movable reference during a particular medical or dental (i.e., surgical) procedure.

Figure 2B:
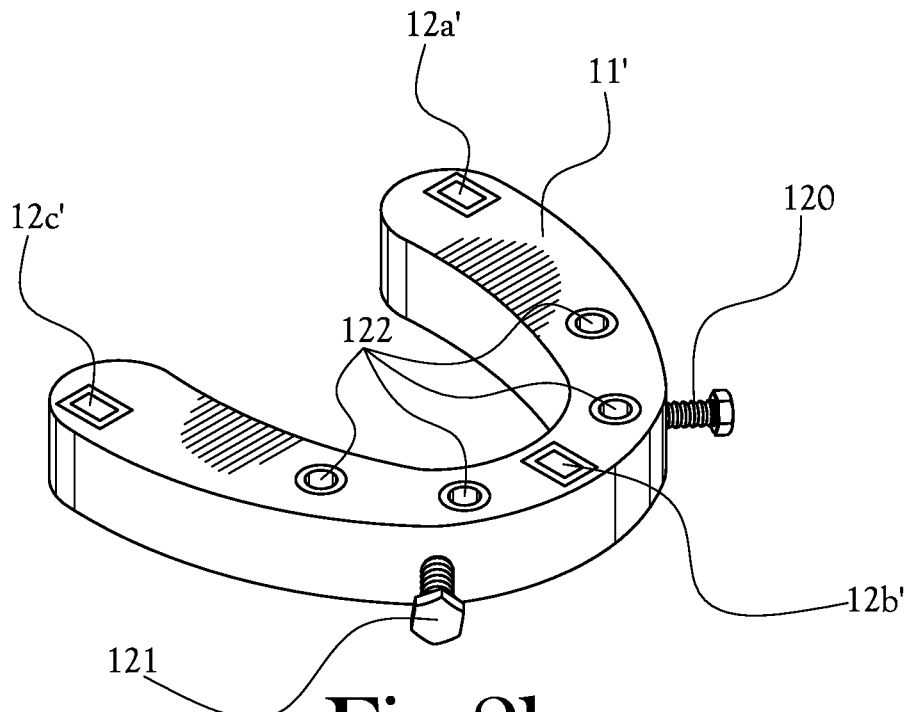
FIG. 2B is a perspective view of an exemplary guide member including electromagnetic sensor members in accordance with another example embodiment of the present general inventive concept.

Referring to FIGS. 2A and 2B, the guide members 11, 11' can be fabricated from a digital scan for use as fixation assist. For example, the guide members 11, 11' can be fabricated from a digital scanner, CT, CBCT, MRI, or similar devices to produce individualized tooth-borne (via tooth cusps) template. Other types of guide members can be used to register other anatomical regions of the body, such as a bone borne template for edentulous mandible, maxilla, spine, hip, etc., or soft tissue templates for radial forearm, nose, ear, or other regions. For example, it is possible to outfit titanium plates/resorbable plates/titanium screws with already pre-slotted intaglio surface for a navigation plate, screw, etc., and to custom fit templates using plate manufacturers. Thus, the techniques and devices of the present general inventive concept are not limited to craniofacial use, but can be applied in dentistry, oral surgery, orthopedics, ENT, neurosurgery, or other surgical fields. The guide members can be sterilized prior to introduction into the operating room, obviating the need for re-sterilization process.

It is also possible to integrate RFID sensors, and/or other types of sensors, such as Bluetooth enabled sensors, into a mesh-like bite plate device, where the sensors are disposed or integrated within the mesh construct of the device itself. The RFID sensors can be powered by solar cells or other energy harvesting devices, such as RF harvesting devices. The integrated device can then be attached to a movable region of interest, such as the patient's lower jaw, to track movements thereof during an operative procedure. The present general inventive concept is not limited to the exemplary configurations illustrated and described herein. To the contrary, a variety of other configurations and combinations of dental/medical devices can be adapted with a variety of different sensor technologies (e.g., swarming technology) to carry out the techniques of the present general inventive concept. For example, it is possible to utilize various combinations of sensor technologies, such as EM and/or optical, during a single operative procedure, depending on the particular components and instruments chosen and adapted for use.

Referring to the example embodiment of FIG. 2A, there is illustrated a perspective view of a typical movable guide member 11 adapted to include an array of sensor members 12a, 12b, and 12c to detect light emitted from the emitting device 17, in accordance with an example embodiment of the present general inventive concept. In this example embodiment, the sensors 12a, 12b, and 12c can function as reflecting markers to transmit light signals received from the emitting device 17 to a detection unit 17c. The detection unit 17c can continuously acquire the position of the sensors 12a, 12b, and 12c and can inform the control unit 16 of the location of the sensors in real time. The control system 16 can compute the position of the movable guide member 11 using a known multi-triangulation method based on information received from the sensors 12a, 12b, and 12c, and can display on display monitor 8 an image displaying the position of the movable guide member 11 with respect to various other components, structures, and reference points of the navigation system 10.

Referring to FIGS. 1 and 2A, the sensors 12a, 12b, and 12c can be configured to extend from an outer surface of the guide member 11 to help maintain consistent line-of-sight between the sensors 12a, 12b, 12c and the light emitting device 17. Although FIGS. 1 and 2A depict an oral surgery configuration, those skilled in the art will appreciate that the present general inventive concept is not limited to the embodiments of FIGS. 1 and 2A, and that many other shapes and sizes of guide members 11 and sensors 12a, 12b, 12c may be used to facilitate mounting of such devices on other parts of the body, internally and externally, and may be used in connection with other types of surgeries where it is useful to maintain a movable reference to help locate surgical instruments or components when the target anatomical structure is moved during surgery.

In the case of dental implants, for example, it is possible to mount a sensor array 12 to the movable guide member 11 to facilitate tracking of the guide member 11 as the mandible is moved, enabling the surgeon to maintain consistent and proper positioning of the surgical component 13 with respect to the mandible even when the mandible is moved during surgery.

In the embodiment of FIG. 1, the surgeon attaches the movable guide member 11 and sensor 12 to the target point, such as the patient's mandible 19 as illustrated in FIG. 1. During a surgical procedure, the control unit 16 can track the location of the movable guide member 11 and the surgical component 13 in real time, enabling the surgeon to maintain proper positioning of the surgical component 13 with respect to the target point even when the movable guide member 11 is moved during surgery.

During a surgical procedure, the surgeon may move the surgical component 13 with respect to the targeted surgical region of the patient, for example the mandible 19 area as illustrated in FIG. 1. As the surgeon is moving the surgical component 13, the control unit 16 can track the location of the surgical component 13 via the sensors 14 mounted on the surgical component 13. The control system 16 can interpret the response signals of the sensor 14 to compute the position of the surgical component 13 using a known multi-triangulation method based on response signals of the sensors 14, and can display on display monitor 8 an image displaying the position of the surgical component 13 with respect to the targeted region of the patient. These techniques enable a surgeon to track the relative positions of the movable guide member 11 and surgical component 13 in the targeted surgical field, even when the movable guide member 11 is moved during the surgical process. Using the present general inventive concepts, it is thus possible to utilize known GPS triangulation methods to determine the location of sensors on both the patient's body and the surgical component, independent of information regarding the shape or size of the sensor to calculation the location thereof.

Referring to FIG. 1, in the case where the emitting device 17 emits infrared light signals, it is important that the sensors 12 and 14 remain in the visual field of the emitted light signals to help produce consistent and accurate locations of the movable guide member 11 and surgical component 13 in the control unit 16 as the surgical component 13 and guide member 11 are moved during surgery. However, in cases where the emitting device does not emit light signals but instead emits EM or other types of RF or wireless signals, it is not as important to maintain the sensors 12 and 14 in the visual line-of-sight of the emitted signals, as EM and other types of RF signals have the ability to penetrate and communicate with sensors that are not directly in the visual line-of-sight of the EM or RF source.

FIG. 2B is a perspective view of guide member including sensor members in accordance with another example embodiment of the present general inventive concept, for example, in a case where the emitting device 17 emits EM or other RF-based signals.

Referring to FIG. 2B, in a case where the emitting device 17 emits EM or other RF-based signals, the sensors of the movable guide member 11' can include an array of detectors, such as radio frequency identification (RFID) sensors 12a', 12b', and 12c', to communicate with the EM signals emitted from the emitting device 17. Unlike the configuration of FIG. 2A, the RFID sensors 12a', 12b', and 12c' can be mounted internally with respect to the guide member 11' as illustrated in FIG. 2B. The RFID sensors can be mounted within the internal structure of the guide member 11' since it is not as important to maintain a direct line-of-sight between the sensors and the emitting device 17 due to the penetrating characteristics of EM and other types of RF signals. In operation, the RFID sensors 12a', 12b', and 12c' function to interact with the electromagnetic field generated by the emitting device 17, and the control unit 16 can recognize any disruptions in the magnetic field caused by the RFID sensors, enabling the system's computer, which has special tracking software, to recognize the location of the RFID sensors and its location in the surgical field using a known multi-triangulation concept based on the interaction of the RFID sensors 12a', 12b', and 12c' with the electromagnetic field. Similar to the embodiment of FIG. 2A, the control unit 16 can compute the position of the movable guide member 11' in real time based on this information, and can display on display monitor 8 an image displaying the position of the movable guide member 11' with respect to various other components, structures, and reference points of the navigation system 10.

Figure 3:
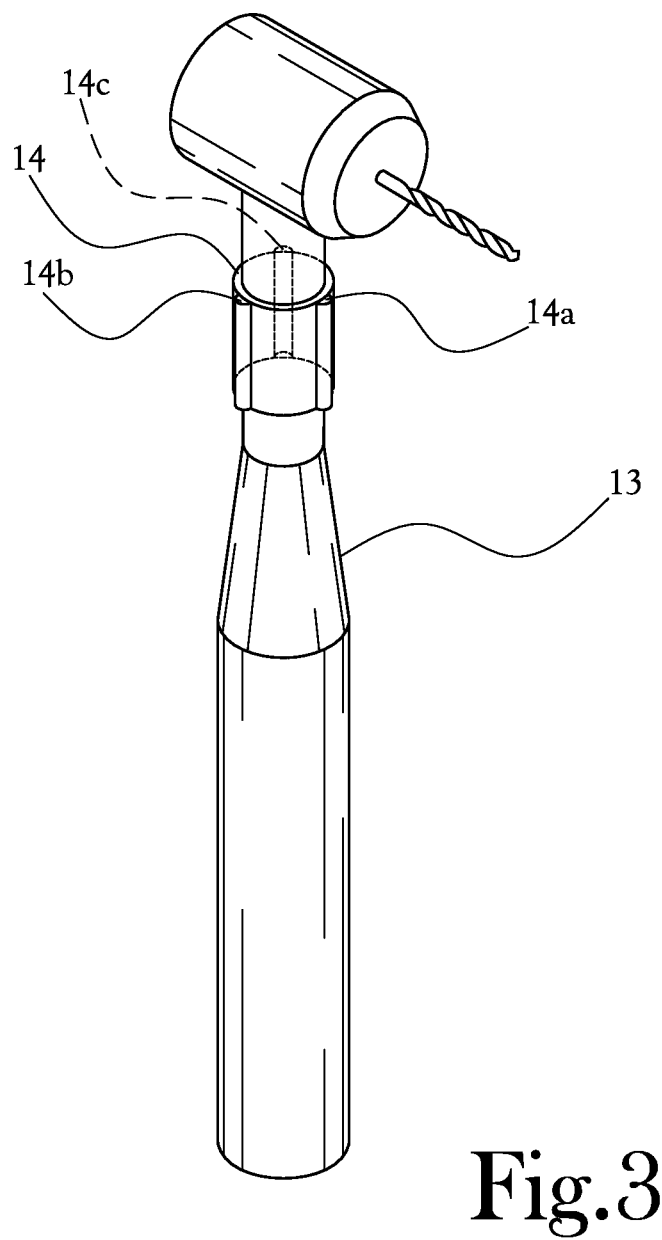
FIG. 3 is a perspective view of a surgical instrument including optical or electromagnetic sensor members in accordance with an example embodiment of the present general inventive concept.

FIG. 3 is a perspective view of an exemplary surgical component 13 including a sensor array 14 configured in accordance with an example embodiment of the present general inventive concept.

Referring to FIG. 3, the surgical component 13 includes a sensor array 14 including sensors 14a, 14b, and 14c. These sensors are configured to respond to propagating signals emitted from the emitting device 17 to track the location of the surgical component in the surgical field, in the manners discussed above. As with sensors 12a, 12b, and 12c, sensors 14a, 14b, and 14c can be configured to interact with LED, EM, Wireless, WiFi, Bluetooth, IR, and/or other types and combinations of wired or wireless signals in known ways to track the location of various components associated with the sensors. The sensors can be powered by solar cells or other energy harvesting devices.

To facilitate attachment of the sensor array 14 to the surgical component, the sensor array may be mounted in the form of a ring-like shape to fit around a shaft or neck region of the surgical component 13, as illustrated in FIG. 3. Such a configuration is easily adaptable to any number of different shaped and sized surgical components. However, those skilled in the art will appreciate that the specific means of mounting the sensors to the various components can be chosen with sound engineering judgment, and a variety of mounting shapes and configurations could be used without departing from the broader scope of the present general inventive concept. For example, the sensors 14a, 14b, and 14c could be integrally mounted and formed in the surgical component 13 as a single body to communicate with the propagating signal without sacrificing proper positioning of the surgical component 13 with respect to the surgical field. Using the responses of the sensors 14a, 14b, and 14c, the control unit 16 can calculate the position of the surgical component 13 relative to the movable reference region and can track and compare the relative movements of the guide member 11 with respect to the surgical component 13. It is possible to include a slot or other type of holding means in one or more of the exemplary devices of the navigation system to hold a microSD card or other memory device to store or upload data to/from the navigation system.

Figure 4:
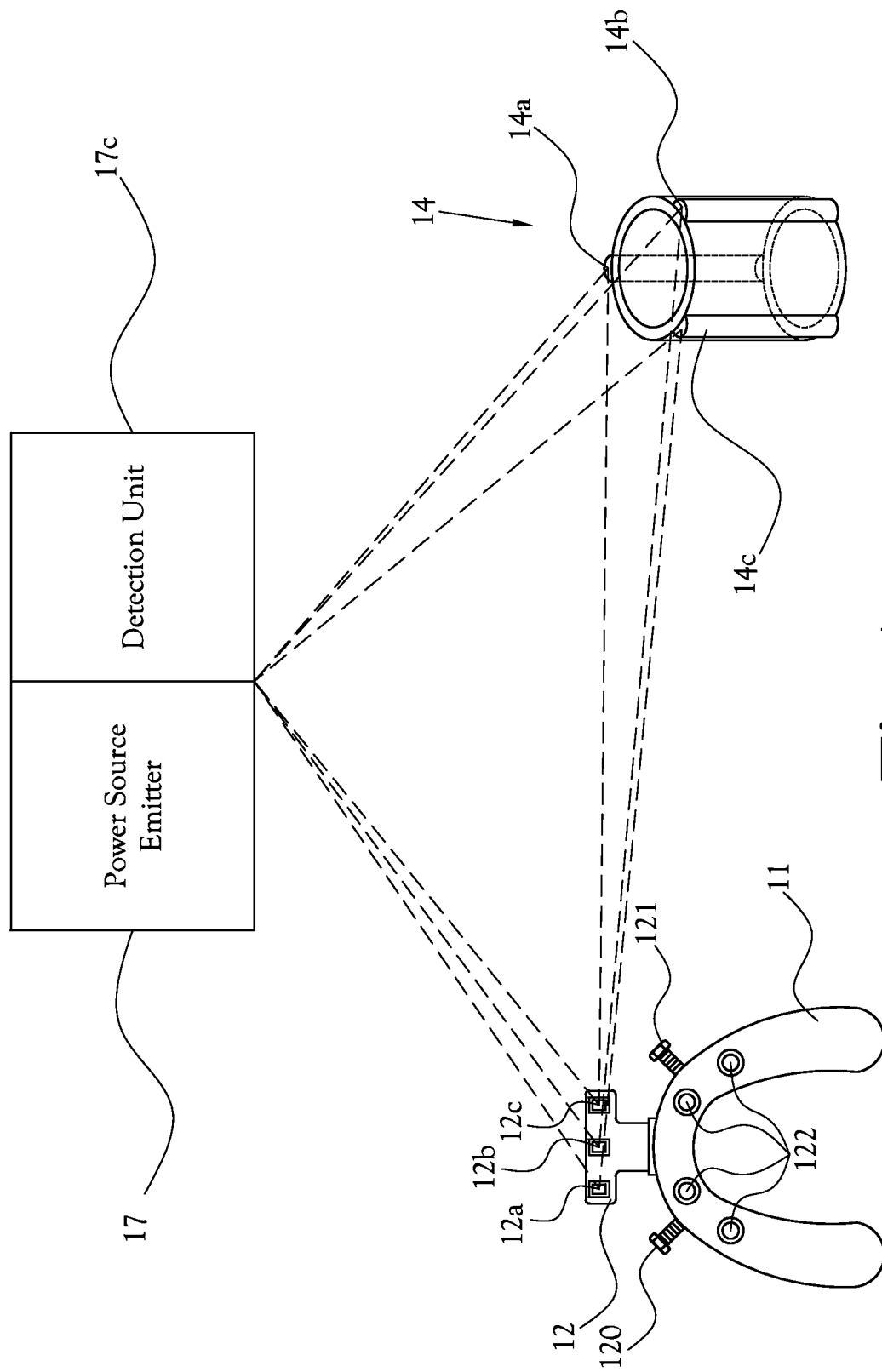
FIG. 4 is a diagram illustrating a power source emitter and detection unit communicating with sensor units configured in accordance with an example embodiment of the present general inventive concept.

Referring to FIG. 4, it is possible to configure the sensors 12 and 14 to communicate with each other, in addition to communicating with the emitter device 17 and/or detection unit 17c, to provide additional information about the relative positions of the respective guide member 11 and surgical component 13. In this regard, the sensors 12 and 14 are not required to be the same or similar types of devices, but instead may be different, wherein the sensors independently interact with one or more of the emitting devices 17 and/or detection unit 17c to track location information of the respective sensors. For example, one of the sensors 12 could be configured to include an EM source and a light reflector sensor, and the other sensor 14 could be configured to include an RFID receptor to interact with the EM field generated by sensor 12. In such a case, the emitter device 17 and detection unit 17c could be adapted to track the location of sensor 12 by characterizing the light reflected by sensor 12, and the control unit 16 could be adapted track the relative distance between the sensors 12 and 14 by detecting disruptions in the EM field caused by movement of the RFID receptor of sensor 14. A variety of other types and combinations of sensors could also be used.

FIG. 4 is a simple diagram illustrating a light source and light detector in communication with sensor arrays 12, 14 in accordance with an example embodiment of the present general inventive concept. In this embodiment, to facilitate GPS triangulation calculations, three points of reference are used, corresponding to three sensors on each device (12a, 12b, 12c and 14a, 14b, 14c). Typically, the sensors 12a, 12b, 12c and 14a, 14b, 14c can communicate with the power source 17 and/or detection unit 17c to provide information regarding the location of the respective devices, as indicated by the dotted lines extending between the sensors and the power source 17 and detection unit 17c. It is also possible that the sensors 12a, 12b, 12c can communicate directly with the other sensors 14a, 14b, 14c to provide information about the relative positions of the devices, as indicated by the dotted lines extending between the sensor arrays 12 and 14. For example, the sensors 12a, 12b, and 12c could be configured to include an EM source to emit a tracking signal to the sensors 14a, 14b, and 14c, and the sensors 14a, 14b, and 14c could be configured to include an RFID receptor configured to interact with the EM field generated by the EM source based on the position of the RFID receptors. Accordingly, disruptions or changes to the EM field caused by movement of the RFID receptors can be detected by the detection unit 17c and fed to the control unit 16 (FIG. 1) to calculate and display location information about the relative positions of the sensors. Moreover, the use of RFID, Bluetooth, IR, EM, LED, or other types of sensors can be interchanged, mixed, or combined for use with different devices and applications, without departing from the broader principles and scope of the present general inventive concept. For example, swarming technology can be used to implement a variety of different sensor technologies (e.g., EM and/or optical) on a variety of different surgical components and regions of interest to track movements thereof during single or multiple operative procedures of a patient.

It is also possible to utilize thermography in conjunction with the navigation techniques of the present general inventive concept to identify other structures in and around the surgical region of interest such as nerves, arteries, veins, and the like. For example, after the RFID sensors track and identify the location of teeth or other structures in a surgical region of interest, such as the mandible, it is possible to identify the location of nerves, arteries, or veins in the mandible using thermography, thus providing additional navigational information to supplement the information provided from the multi-triangulation techniques of the present general inventive concept. In other words, it is possible to incorporate thermal imaging cameras into, or in combination with, the exemplary sensors of the present general inventive concept in order to detect variations in the infrared radiation of various body parts and to display thermographic images thereof. In this way, if the surgeon knows that the artery, vein, or nerve runs along with the vein, the use of thermography can be used to identify where the canal is, thus providing additional location information in addition to the information provided by the RFID or other sensors. Accordingly, not only can the multi-triangulation concepts of the present general inventive concept be used to indicate where a boney indentation is in the bone, but thermography concepts can also be incorporated into the navigation system of the present general inventive concept to help identify and locate the nerve, artery, and/or vein during surgery.

Figure 5:
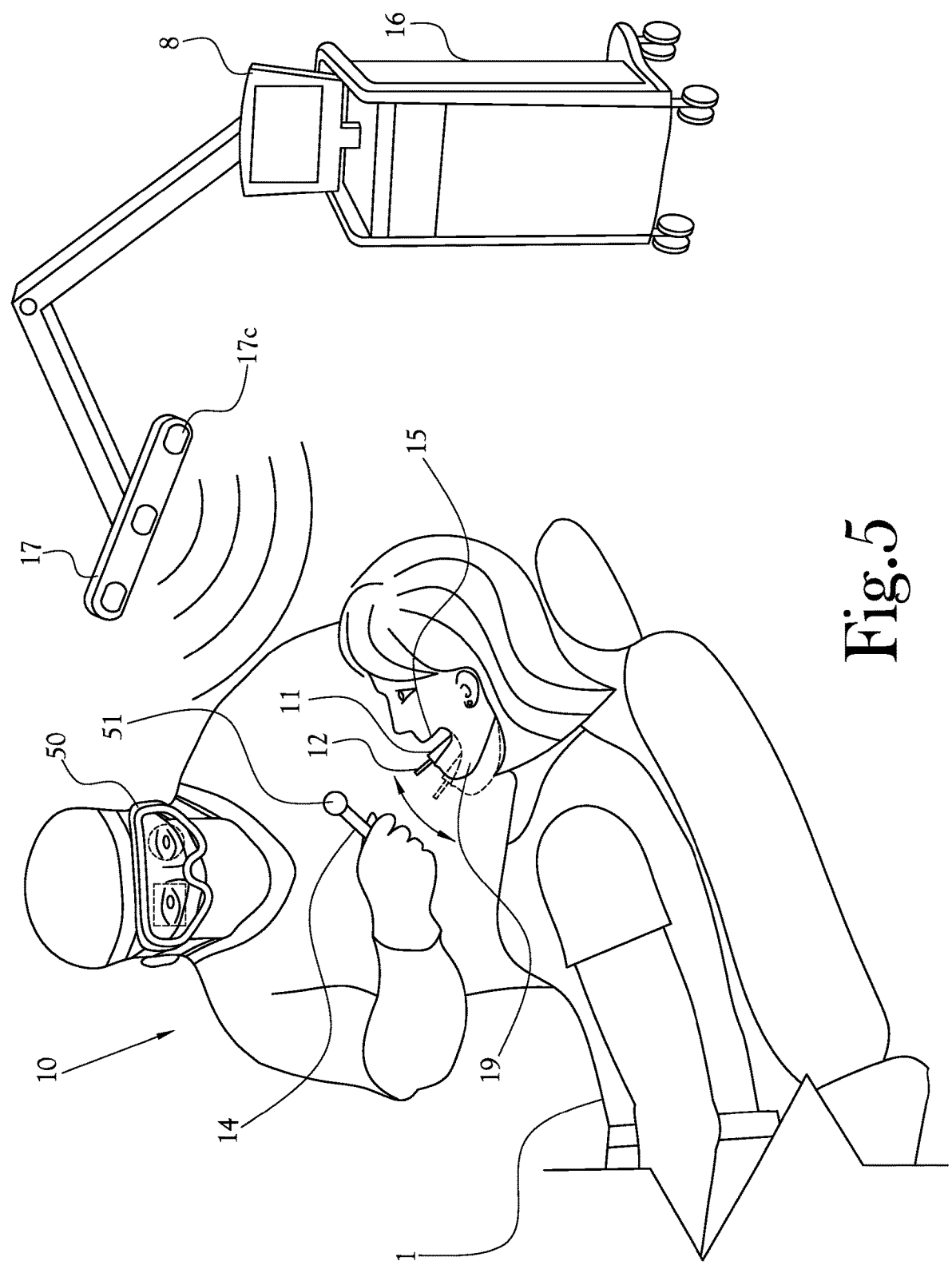
FIG. 5 is a perspective view of a system environment including a scanning wand and navigation goggles for use in accordance with example embodiments of the present general inventive concept.

FIG. 5 is a perspective view of a system environment including a pair of navigation goggles 50 and a digital scanning wand 51 for use in accordance with example embodiments of the present general inventive concept. The scanning wand 51 can be used to superimpose measurements onto the patient scan data, such as CT scan data. The measurements from the scanning wand 51 can be used to supplement or replace patient scan data to enable the surgeon to determine location information of surgical sites of interest that may be modified or moved relative to the original scan data. For example, the navigation goggles 50 can interface with the navigation system, via a wired or wireless connection, to enable the surgeon to visualize location information of surgical sites of interest in real time during surgery.

Figure 6:
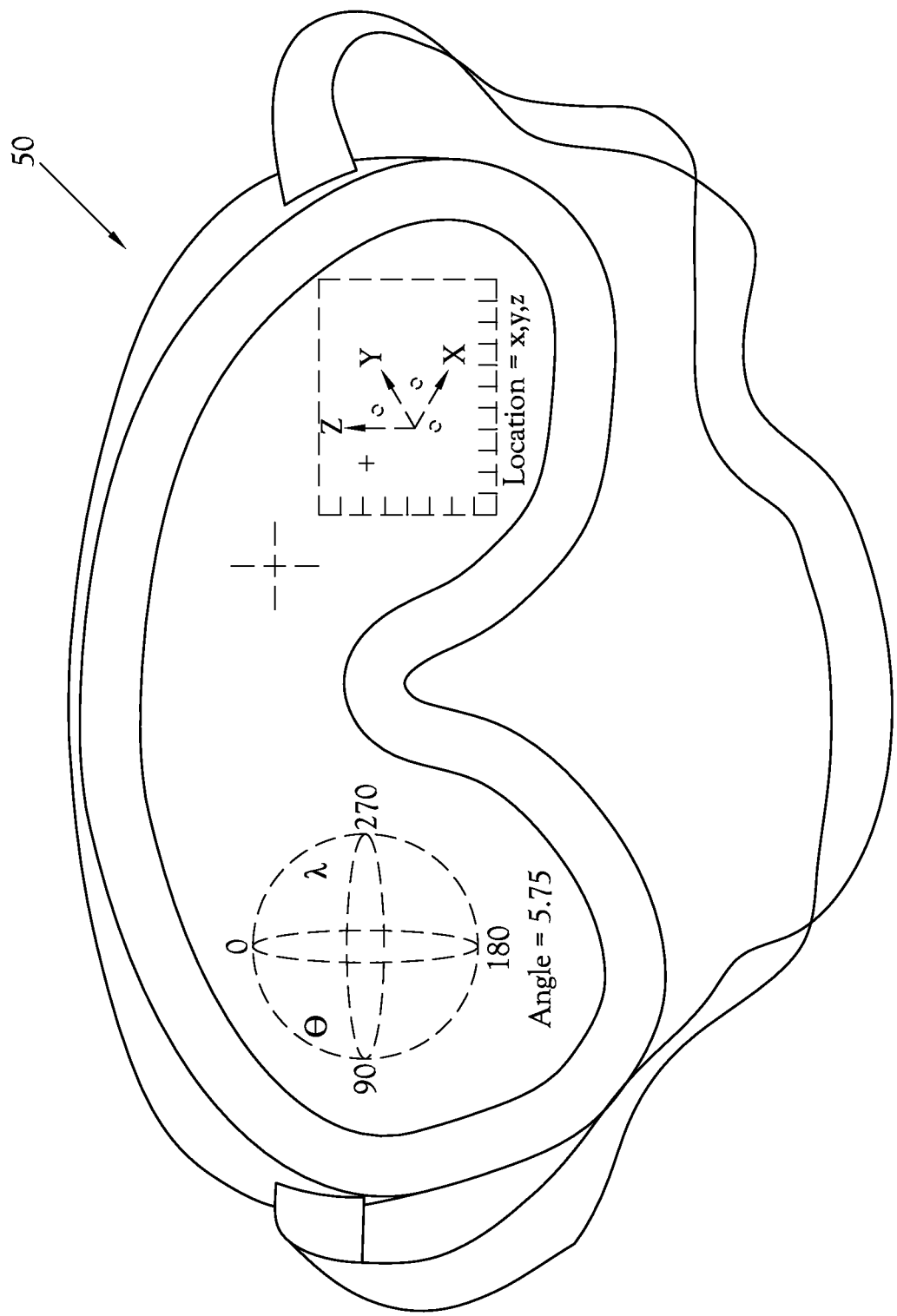
FIG. 6 illustrates an exemplary set of navigation goggles configured in accordance with an example embodiment of the present general inventive concept.

FIG. 6 illustrates an exemplary set of navigation goggles 50 configured in accordance with an example embodiment of the present general inventive concept. Referring to FIG. 6, the goggles 50 facilitate 3D viewing of the surgical field with an overlay of the scan. The goggles can include sensors to sense the blinking of the eyelids and eye movements to function in part with verbal commands and buttons on the instruments to control various aspects of the surgical field including the 3D viewing experience of the goggles. The goggles 50 can include various overlays to display navigation data, such as location of surgical components and/or surgical sites in 3-dimensional space, angular information, target points, and the like. Thus, the location information provided by the navigation system can processed and fed to the navigation goggles 50 in various forms to assist the surgeon in visualizing and locating surgical components and surgical sites as the operation is being performed. For example, it is possible for the surgeon to visualize tumors or other surgical sites, to see the depths of invasion, and to superimpose data from the digital wand and/or CT scan while cutting or performing other operations on the patient.

Figure 7:
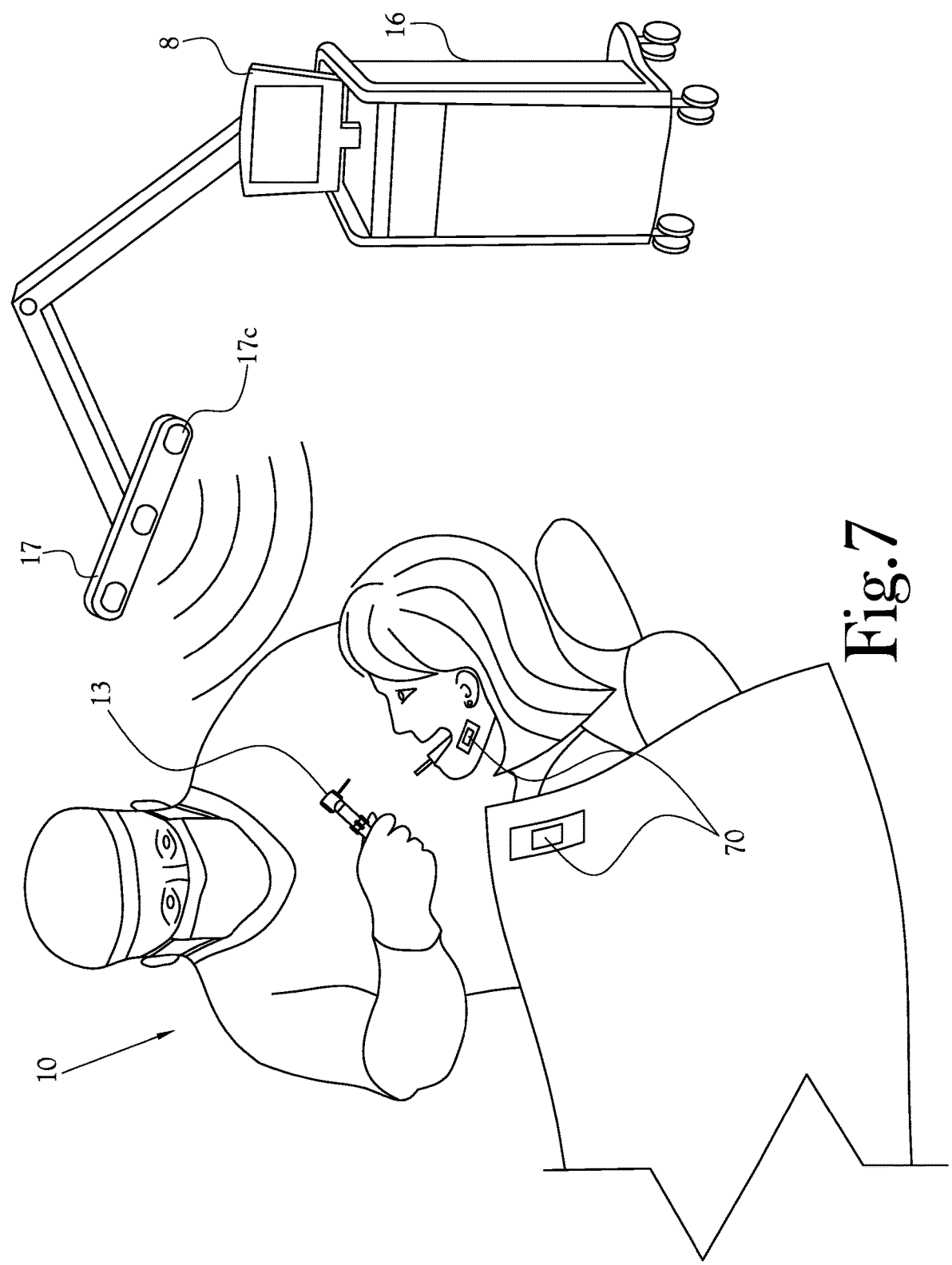
FIG. 7 is a perspective view of a system environment including dressings configured for use in accordance with example embodiments of the present general inventive concept.

FIG. 7 is a perspective view of a system environment including exemplary dressings 70 configured for use in accordance with example embodiments of the present general inventive concept. Similar to the surgical components 13 and guide members 11, the dressings 70 can include suitable sensors, such as RFID sensors, to communicate location information concerning the placement of the dressings 70. The dressings 70 can be placed to reference various aspects of surgical and non-surgical wound dimensions, wherein the wounds orientation and sensors are able to detect the condition of the wound in conjunction with navigation. The dressings 70 can include a solar cell or other energy harvesting device to power the sensors, but the present general inventive concept is not limited to any particular type of sensor or power source. Thus, by strategically placing one or more dressings 70 at various locations of interest on or around the patient, location information can be communicated from the dressings 70 to the navigation system using GPS triangulation techniques relative to the sensors of each dressing, thus providing location information of each dressing relative to other surgical components or surgical sites of interest. The location information can then be processed by the control unit and displayed in various formats to the surgeon via display monitor 8 (FIG. 1) and/or navigation goggles 50 (FIG. 6).

Figure 8:
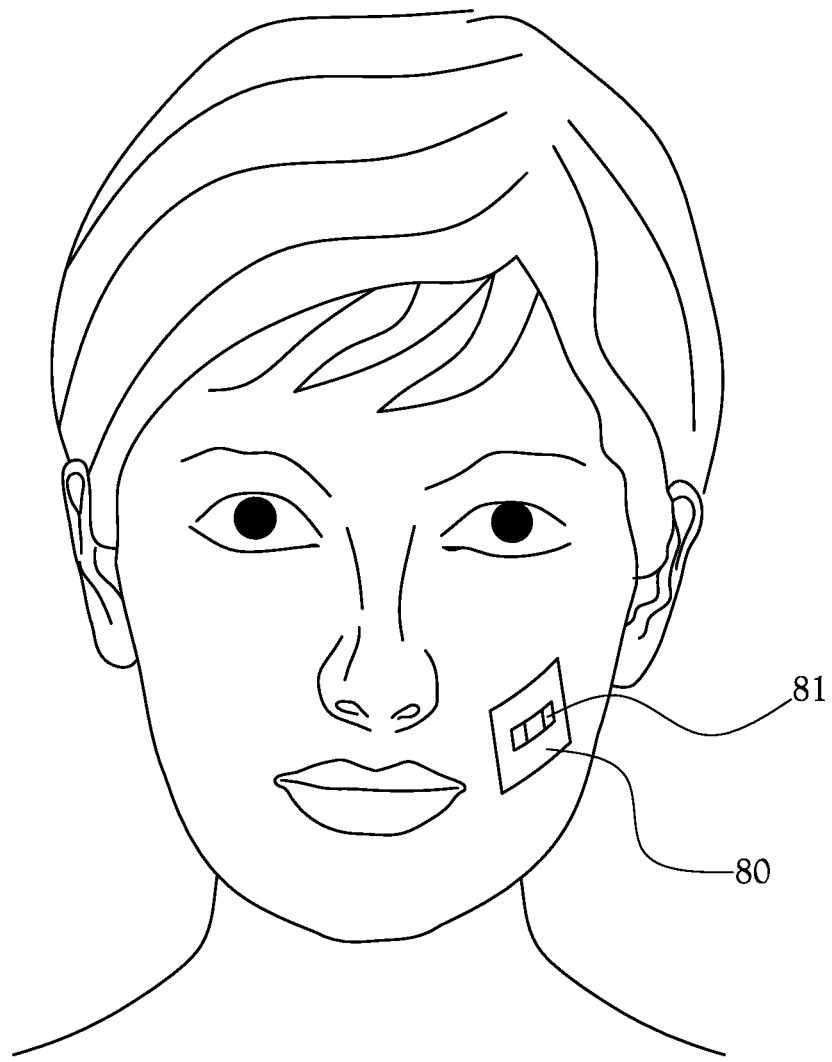
FIG. 8 illustrates an exemplary wound dressing configured in accordance with an example embodiment of the present general inventive concept.

FIG. 8 illustrates an exemplary wound dressing 80 including a tripartite sensor arrangement (similar as described above) to facilitate GPS triangulation calculations and location data of the dressing 80 relative to other surgical components, surgical sites, and/or other anatomical regions of interest.

FIG. 9 illustrates an exemplary wound dressing 90 including a plurality of treatment devices to aid in the navigation, detection, and/or treatment of a variety of parameters to assist in operations of a wound or surgical site, according to an example embodiment of the present general inventive concept. Exemplary treatment devices are illustrated in a circuit fashion in FIG. 9, with a key indicating some exemplary parameters for use of the treatment devices, although the present general inventive concept is not limited to the illustrated parameters, and a variety of other parameters could be used without departing from the scope and spirit of the present general inventive concept.

The treatment devices of FIG. 9 can be implemented in combination with RFID or other navigation sensors to provide navigation and treatment information respecting a particular wound. For example, as illustrated in FIG. 9, it is possible to provide one or more gas sensors to detect gases such as NO, $O_2$, $CO_2$, or other gases in or around a particular wound area. This information can be communicated to the navigation system to provide a monitoring component of a particular wound area. Other parameters can also be monitored, for example, temperature, pH, bacteria level, pressure, and the like. It is also possible to provide one or more ultraviolet (UV) devices to detect and/or deliver UV energy to targeted areas of the wound, based on results of the other parameter measurements and/or detections. Treatment devices may also be targeted to various regions of the dressing using navigation information provided by RFID or other GPS devices of the wound dressing.

While the present general inventive concept has been illustrated by description of example embodiments and while the illustrative embodiments have been described by referring to the drawings, it is not the intention of the applicant to restrict or in any way limit the scope of the appended claims to the illustrative examples. Additional advantages and modifications of the present general inventive concept will readily appear to those skilled in the art. The present general inventive concept in its broader aspects is therefore not limited to the specific details, representative apparatus and methods, and illustrative examples illustrated and described. Accordingly, departures may be made from such details without departing from the spirit or scope of applicant's general inventive concept.

What is claimed is:

1. A navigation system to track positions of surgical components during surgery of a patient, comprising:
   a power source to emit a tracking signal during surgery of a patient;
   a first sensor configured to be mounted to a region of the patient to generate a first response signal to the emitted tracking signal;
   a second sensor configured to be mounted to a surgical component to generate a second response signal to the emitted tracking signal;
   a control unit to track a position of the surgical component relative to the region as the surgical instrument and region move with respect to a fixed region of the patient, the control unit configured to receive the first response signal and the second response signal, the control unit configured to determine the real-time tracked position in three dimensional space of the region based on the first response signal, and configured to determine the real-time tracked position in three dimensional space of the surgical component based on the second response signal,
   a display monitor configured to display a real time position of the region and the fixed region,
   wherein the tracked position is based on a triangulation calculation relative to the first and second response signals independent of a shape dimension of the first and second sensors, and
   navigation goggles configured to be worn by a surgeon to interface with the control unit of the navigation system via a wired or wireless connection to receive and display in real-time the navigational data including the location of the surgical component and/or target points in the region during surgery based on the first and second response signals, the display of the navigational data in the goggles being provided as an overlay so as not to inhibit viewing by the surgeon through the googles.

2. The navigation system of claim 1, wherein the first sensor is fabricated from a digital scanner to read data pertaining to a region of interest of the patient to adjust existing CT scan data of the patient.

3. A navigation system to track positions of surgical components, comprising:
   a power source to emit a tracking signal during an operation of a patient;
   a first component configured to be mounted to a region of interest of the
   patient, the first component including a first sensor to respond to the emitted tracking signal to provide location information of the first component;
   a second component including a second sensor to respond to the emitted tracking signal to provide location information of the second component; and
   a control unit to track the locations of the first and second component relative to a fixed region of the patient as the first or second components move with respect to the fixed region based on the responses of the first and second sensors, independent of a shape dimension of the first or second sensors, the control unit configured to receive the first and second response signals, the control unit configured to determine the real-time tracked position in three dimensional space of the first component relative to the fixed region based on the first response signal, and configured to determine the real-time tracked position in three dimensional space of the second component relative to the fixed region based on the second response signal,
   wherein the first component comprises a dressing to cover a wound of a patient, the dressing including at least one detector to measure a characteristic parameter of the wound and to transmit a signal representative of the measured characteristic parameter to the control unit, the control unit being configured to receive the transmitted signal and to output a response indicative of the measured characteristic parameter to treat the wound; and
   navigation goggles configured to be worn by a surgeon to interface with the control unit of the navigation system via a wired or wireless connection to receive and display in real-time the navigational data including the location of the surgical component and/ or target points in the region during surgery based on the first and second response signals, the display of the navigational data in the googles being provided as an overlay so as not to inhibit viewing by the surgeon through the googles.

4. The navigation system of claim 3, wherein the dressing includes at least one delivery device to deliver a treatment element to a selected region of the wound based on a location of the measured characteristic parameter.

5. The navigation system of claim 3, further comprising an energy harvesting device to power the at least one detector and the at least one delivery device.

6. The navigation system of claim 1, wherein the first sensor comprises an emitting unit to emit a second tracking signal to the second sensor, and the second sensor comprises a receptor unit to respond to the second tracking signal such that the control unit tracks the movement of the surgical component relative to the movable region based on the response of the receptor unit to the second tracking signal.

7. The navigation system of claim 1, further comprising a surgical aid component configured to be mounted to the region.

8. The navigation system of claim 7, wherein the first sensor is coupled to an outer surface of the surgical aid component and is oriented during use to maintain a visible line of sight with the emitted signals as the region moves with respect to the fixed region during the surgical process.

9. The navigation system of claim 1, wherein the first sensor comprises at least three RFID, Bluetooth, LED, or WiFi receptors to interact with the emitted tracking signals, and the control unit tracks the position of the region using the triangulation calculation based on the interaction of the at least three receptors.

10. The navigation system of claim 1, wherein the first and second sensors each comprise at least three optical emitters to respectively emit first, second, and third light signals to be detected by the detection unit, such that the control unit tracks the position of the surgical component relative to the movable region using the triangulation calculation based on the detected first, second, and third light signals.

* * * * *